United States Patent
Maytal et al.

[11] Patent Number: 5,978,697
[45] Date of Patent: Nov. 2, 1999

[54] SYSTEM AND METHOD FOR MRI-GUIDED CRYOSURGERY

[75] Inventors: Ben-Zion Maytal, Atlit; Mordechai Bliweis, Haifa; Gideon Even Sturlesi, Cammon, all of Israel

[73] Assignee: Galil Medical Ltd., Yokneam, Israel

[21] Appl. No.: 09/002,923

[22] Filed: Jan. 5, 1998

[51] Int. Cl.$^6$ ..................................................... A61B 5/055
[52] U.S. Cl. ........................................... 600/411; 324/320
[58] Field of Search ..................................... 600/411, 549, 600/410; 324/320; 62/51.2, 50.1, 50.2; 606/20, 21; 335/216

[56] References Cited

U.S. PATENT DOCUMENTS

| | | | |
|---|---|---|---|
| 5,357,958 | 10/1994 | Kaufman | 600/417 |
| 5,431,164 | 7/1995 | Westphal et al. | 600/410 |
| 5,432,544 | 7/1995 | Ziarati | 348/61 |
| 5,531,742 | 7/1996 | Barken | 606/21 |
| 5,647,361 | 7/1997 | Damadian | 604/27 |
| 5,682,890 | 11/1997 | Kormos et al. | 600/417 |
| 5,733,247 | 3/1998 | Fallon | 600/410 |

*Primary Examiner*—Brian L. Casler
*Attorney, Agent, or Firm*—Mark M. Friedman

[57] ABSTRACT

System and method for performing MRI-guided cryosurgery are provided. The system includes: (a) an MRI magnet for accommodating a patient, the MRI magnet having at least one opening for enabling access of a surgeon to the patient, the MRI magnet including at least one channel extending therethrough for receiving a line member of a surgical device; (b) a surgical device, including: (i) an operating member for operating the patient; (ii) a control member for controlling the operating member, the control member being positioned externally to the MRI room; (iii) a line member having a first end connectable to the operating member and a second end connectable to said control member, wherein at least a portion of the line member is received within the channel of the MRI magnet. Preferably, the line member includes an underground portion extending through an underground channel. The MRI magnet may include an interface member for connecting the operating member thereto. Preferably, the operating member is a cryogenic probe including a Joule-Thomson heat exchanger, the line member is a gas tube, and the control member includes a gas container for providing high pressure gas to the cryogenic probe via the gas tube. Preferably, the control member includes a microprocessor for controlling the operation of said surgical device.

10 Claims, 2 Drawing Sheets

SYSTEM AND METHOD FOR MRI-GUIDED CRYOSURGERY

FIELD AND BACKGROUND OF THE INVENTION

The present invention relates to system and method for MRI (Magnetic Resonance Imaging)-monitored and guided cryosurgery. More particularly, the present invention relates to system and method which enable a surgeon to safely and conveniently perform a relatively complicated cryosurgery procedure under the influence of an open MRI magnet, and to obtain accurate and artifacts-free imaging results, thereby enabling effective guidance of the cryosurgery procedure.

MRI-monitored and guided surgical procedures are currently performed by using an "open MRI" apparatus, wherein the MRI magnet includes apertures so as to enable access of a surgeon to the patient.

However, the surgical process within such MRI environment is susceptible to the strong magnetic field of the MRI magnet (about 0.5–2 Tesla). Therefore, the range of surgical tools which may be used within he MRI room is substantially limited.

Various attempts have been made to provide surgical methods and devices which are unsusceptible to the magnetic field of the MRI magnet o as to enable a surgeon to perform substantially complicated surgical procedures within the MRI room.

Most of such attempts are directed toward the development of surgical tools made of compatible materials which are not influenced by the magnetic field of the MRI magnet and which enable to minimize the creation of artifacts interfering with the imaging results.

However, the prior art fails to provide method and device for carrying out an effective MRI-guided cryosurgery procedure.

Currently, cryosurgery procedures are performed by using a liquid nitrogen. The application of such liquid nitrogen to MRI guided cryosurgery requires the positioning of liquid nitrogen containers and appropriate control system within the MRI room, thereby exposing such cryosurgery system to the strong influence of the MRI magnet.

The extent to which such liquid nitrogen cryosurgery system can be kept away from the MRI magnet is substantially limited, since the tubes which supply liquid nitrogen from the containers to the operating tip tend to freeze and rigidify, thereby substantially limiting the manipulation of the operating tip by the surgeon. Therefore, MRI-guided cryosurgery procedures which apply liquified gas such as liquid nitrogen are substantially limited and almost impossible.

There is thus a widely recognized need for, and it would be highly advantageous to have, system and method for MRI-guided cryosurgery which enable a surgeon to safely and conveniently perform an MRI procedure.

There is further a recognized need for such system and method which enable a surgeon to perform a substantially complicated cryosurgery procedure which is unsusceptible to the influence of an MRI magnet, and which enable to obtain accurate and artifacts-free imaging results.

SUMMARY OF THE INVENTION

According to the present invention there is provided a system for MRI-guided cryosurgery, comprising: (a) an MRI magnet for accommodating a patient, the MRI magnet having at least one opening for enabling access of a surgeon to the patient, the MRI magnet including at least one channel extending therethrough for receiving a line member of a surgical device; (b) a surgical device, including: (i) an operating member for operating the patient; (ii) a control member for controlling the operating member, the control member being positioned externally to the MRI room; (iii) a line member having a first end connectable to the operating member and a second end connectable to said control member, wherein at least a portion of the line member is received within the channel of the MRI magnet.

Preferably, the line member includes an underground portion extending through an underground channel.

The MRI magnet may include an interface member for connecting the operating member to said portion of the line member received within said channel.

According to further features in preferred embodiments of the invention described below, the operating member is a cryogenic probe including a Joule-Thomson heat exchanger, the line member is a gas tube, and the control member includes a gas container for providing high pressure gas to the cryogenic probe via the gas tube. Preferably, the control member includes a microprocessor for controlling the operation of said surgical device.

A system according to the present invention further includes a display member positioned within the MRI room, the display member being electrically connected to the microprocessor for providing information relating to the operation of said surgical device.

According to still further features of the preferred embodiments, the cryogenic probe includes a thermal sensor electrically connected to the microprocessor. Further, the cryogenic probe includes at least one switching element for controlling the operation of the cryogenic probe, said at least one switching element being electrically connected to the microprocessor.

Further according to the present invention there is provided a method of MRI-guided cryosurgery, comprising: (a) providing a cryosurgery device, including: (i) a cryogenic probe for operating a patient, the cryogenic probe including a Joule Thomson heat exchanger; (ii) a control member for controlling the operation of said cryogenic probe, the control member including a gas container for providing high pressure gas to the cryogenic probe; and (iii) a gas tube for providing gas communication between the cryogenic probe and the gas container; (b) locating the cryogenic probe within an MRI room, locating the control member externally to the MRI room, and locating at least a portion of the a gas tube within a channel extending through an MRI magnet; (c) connecting the cryogenic probe to said portion of the gas tube located within the channel by means of an interface element.

According to further features in preferred embodiments of the invention described below, the method further comprising monitoring the operation by means of a display member located within the MRI room, the display member providing information relating to the cryogenic probe.

Further according to the present invention there is provided an MRI magnet for accommodating a patient, the MRI magnet being located within an MRI room, said MRI magnet having at least one opening for enabling access of a surgeon to the patient, said MRI magnet including at least one channel extending therethrough for receiving a portion of a surgical device therein, the surgical device for operating the patient. Preferably, the at least one channel extends from a first spot located substantially adjacent the floor of the MRI room to a second spot located substantially above the first spot. The second spot may include an interface member for connecting a surgical member thereto. Preferably, the at least one channel communicates with an underground channel extending from the first spot to a third spot located externally to the MRI room.

The present invention successfully addresses the shortcomings of the presently known configurations by providing system and method for MRI-guided cryosurgery wherein the MRI magnet includes channels for installation of connecting tubes therein so as to enable to directly connect an operating member to the MRI magnet, thereby enabling a surgeon to conveniently and safely handle and the operating members.

Further, the present invention addresses the shortcomings of the presently known configurations by providing system and method for MRI-guided cryosurgery wherein the control unit of the cryosurgery device is located externally to the MRI room, thereby rendering the device unsusceptible to the magnetic field of the MRI magnet.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of system and method for MRI-guided cryosurgery which enable a surgeon to safely and conveniently perform a cryosurgery procedure under the influence of an MRI magnet.

The principles and operation of apparatus and method according to the present invention may be better understood with reference to the drawings and the accompanying description.

Figure 1:
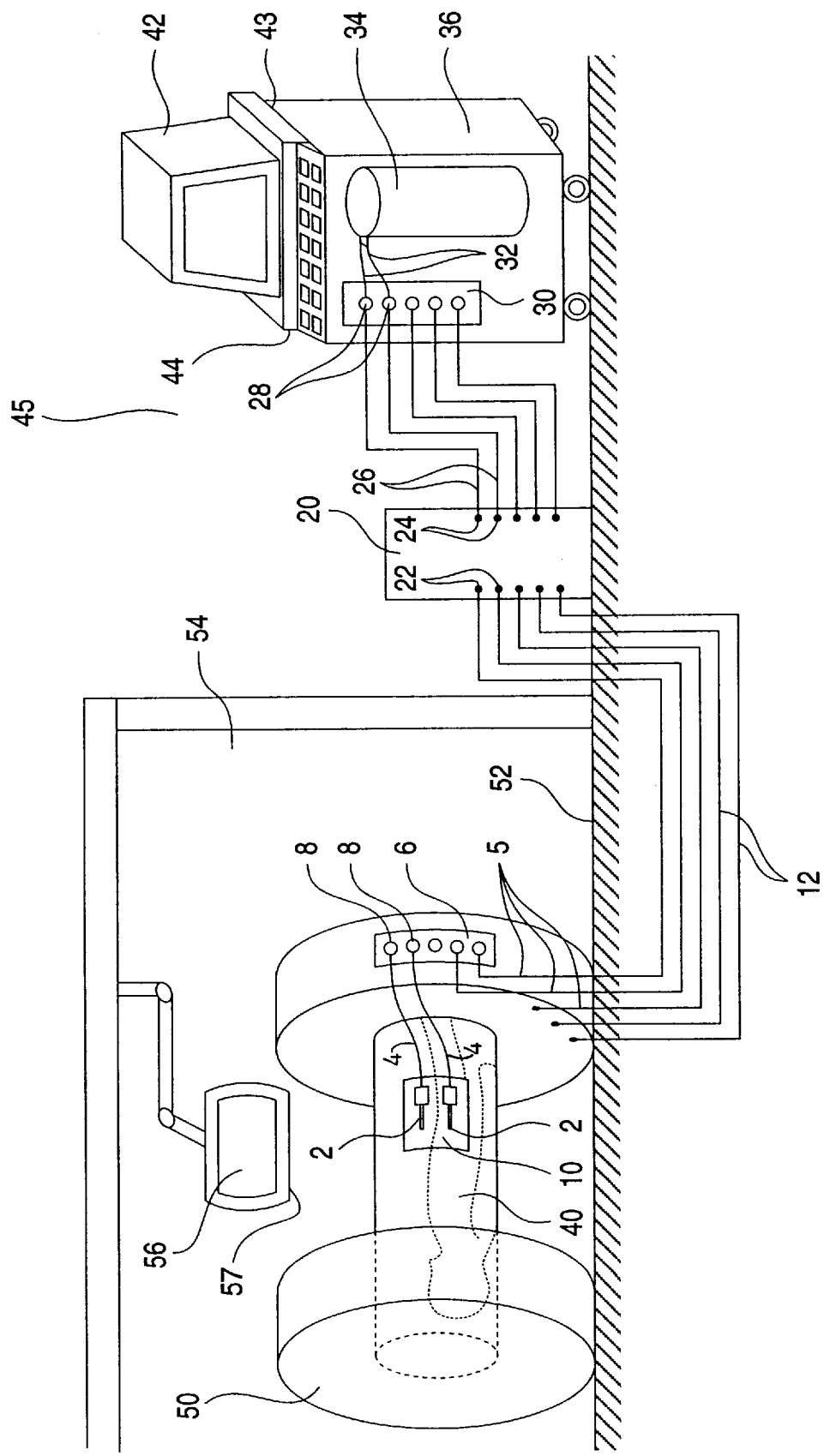
FIG. 1 is a schematic view of an MRI-guided cryosurgery system according to the present invention.

Referring now to the drawings, FIG. 1 illustrates a preferred embodiment of a system according to the present invention.

As shown in the figure, a system according to the present invention includes an "open" MRI magnet 50 for accommodating a patient 40, the MRI magnet including at least one aperture 10 for allowing access of a surgeon to the patient. Magnet 50 includes at least one channel so as to enable installation of electrical and/or mechanical connecting lines such as gas tubes generally denoted as 5 within the MRI magnet. As shown in the figure, connecting lines 5 terminate at interface element 6 which includes a plurality of connecting sites 8 for connecting surgical tools thereto.

Preferably, a plurality of cryosurgery operating members 2 for operating a patient are connected to connection sites 8, the operating members being remotely controlled by a remote control unit 45 located externally to MRI room 54. Each of operating members 2 preferably includes a Joule-Thomson heat exchanger for effectively cooling the operating member.

An underground passageway including underground connecting lines 12 connectable to lines 5 extends from MRI magnet 50 to control unit 15 located externally to MRI room 54. As shown in the figure, connection lines 12 are preferably connected to an immobilized linking box 20 located externally to MRI room 54 via a first set of connection sites 22.

Thus, linking box 20 includes a first set of connection sites 22 for receiving a set of connecting lines 12, and a second set of connection sites 24 for receiving a set of gas tubes 26 arriving from the control unit 45 of the cryosurgery device. Gas tubes 26 are preferably flexible and detachably connected to linking box 20 and control unit 45 of the cryosurgery device.

Preferably, control unit 45 includes a mobile housing 36 for accommodating at least one gas container 34, the gas container for providing a specific gas of high pressure to operating members 2. As shown, housing 36 includes an interface element 30 having connection sites 28 for communicating gas lines 32 arriving from gas container 34 with flexible gas lines 26. Gas container 34 may include a cooling gas such as argon, nitrogen, air, krypton, $CF_4$, xenon, or $N_2O$. A second gas container 34 may be provided for a heating gas such as helium.

Figure 2:
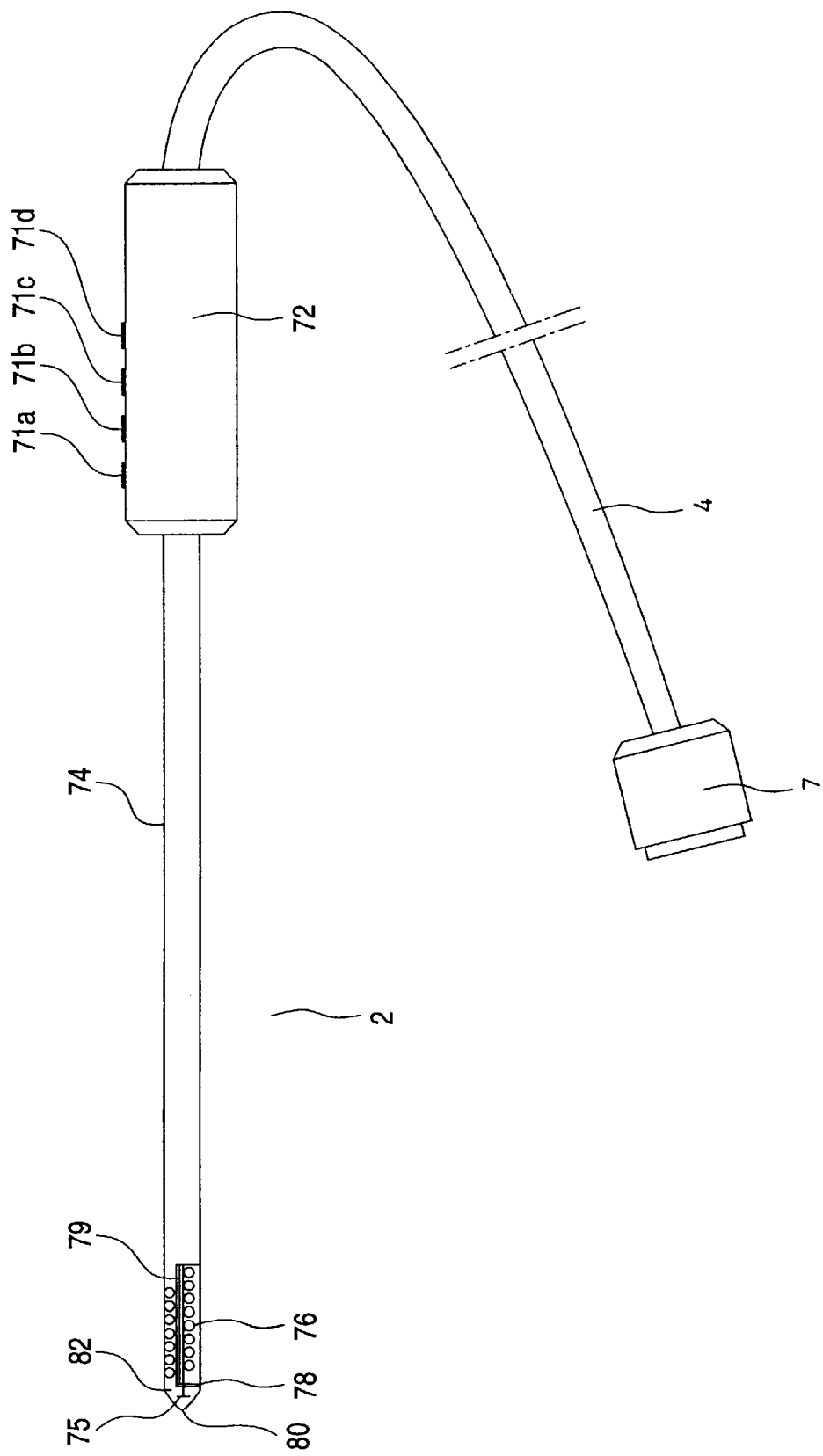
FIG. 2 is a schematic side view, partially in longitudinal section, of an operating tip according to the present invention.

Referring now to FIG. 2, a cryosurgery device according to the present invention preferably applies a Joule-Thomson heat exchanger.

As shown, an operating member 2 according to the present invention includes an elongated operating tip 74 for freezing a patient's tissue. Operating tip 74 includes at least one passageway 76 extending therethrough for providing gas of high pressure to a heat exchanger and an orifice 78 located at the end of operating tip 74, the orifice for passage of high pressure gas therethrough so as to heat or cool operating tip 74, depending on the type of gas used. Gases which may be used for cooling include argon, nitrogen, air, krypton, $CF_4$, xenon, or $N_2O$. Gases which may be used for heating include helium.

When a high pressure gas such as argon flows through the heat exchanger and expands through orifice 78 it liquifies so as to form a cryogenic pool within chamber 82 of operating tip 74, which cryogenic pool effectively cools surface 80 of operating tip 74. The surface 80 of operating tip 74 is preferably made of a heat conducting material such as metal for effectively freezing the patient's tissue. When a high pressure gas such as helium expands through orifice 78 it heats chamber 82, thereby heating surface 80 of the operating tip.

Operating tip 74 includes at least one evacuating passageway 79 extending therethrough for evacuating gas from the operating tip to atmosphere. As shown in the figure, passageway 76 is preferably in the form of a spiral tube wrapped around passageway 79.

Further, operating tip 74 includes at least one thermal sensor 75 for sensing the temperature within chamber 82, the wire of which extending through evacuating passageway 79 or a separate passageway.

Operating tip 74 is connected to a holding member 72 for holding by a surgeon. Holding member 72 includes a plurality of switches 71a, 71b, 71c and 71d for manually controlling operating tip 74 by a surgeon. Switches 71a, 71b, 71c and 71d may provide functions such as on/off, heating, cooling, and predetermined cycles of heating and cooling by selectively and controllably communicating passageway 76 with an appropriate gas container 34 including a cooling or a heating gas.

As shown in FIG. 1, each of operating members 2 is connected via a flexible connecting line 4 to a connecting site 8 on interface element 6. Preferably, each of operating members 2 includes a linking element 7 for attachment to a connection site 8.

Preferably, evacuating passageway 79 extends through connecting line 4 such that the outgoing gas is evacuated through an opening located at linking element 7.

As shown in FIG. 1, positioned on housing 36 are a microprocessor 43, a display element 42, and a keyboard 44. Microprocessor 43 controls the operation of the cryosurgery device according to predetermined operating conditions provided by the surgeon. Keyboard 44 may be used for programming the operating conditions and for reading selected data. Display element 42 is used for displaying data relating to the status of each of the operating members 2 and other updated data on the surgery being performed. Further, display element 42 may provide information relating to the medical record of a specific patient.

Switches 71a, 71b, 71c and 71c of operating member 2 (FIG. 2) are electrically connected to microprocessor 43 so as to enable manual control of operating tip 74. Further, thermal sensor 75 is electrically connected to microprocessor 43 so as to enable continuous monitoring and control of the temperature within chamber 82. A preferred embodiment for providing controlled temperature changes within chamber 82 is disclosed in U.S. Pat. No. 5,540,062. Further features of a cryosurgery device according to the present invention including specific features of control unit 45 and operating member 2 are disclosed in U.S. Pat. Nos. 5,522,870 and 5,603,221.

As shown in FIG. 1, a preferably conventional MRI display element 56 is positioned within MRI room 54 for displaying an image representing the site of operation so as to provide guidance to a surgeon. According to the present invention display element 56 preferably includes a video card and is electrically connected to microprocessor 43 located externally to MRI room 54 via an electrical connection (not shown), which electrical connection may be extended through underground lines 12 and linking box 20. Such configuration enables to provide the surgeon an image identical to the image displayed on external display element 42, which image including information relating to the operation of the cryosurgery device. Display element 56 is provided with a switching member 57 for enabling a surgeon to select the required image and thus to monitor the progress of the surgical process via first and second channels, wherein the first channel provides an MRI guidance and the second channel provides current information relating to the cryosurgery device. According to another embodiment (not shown), a second display element is provided within MRI room 54 so as to enable a surgeon to simultaneously monitor the surgical process and observe the operation of the cryosurgery device.

System and method according to the present invention enable a surgeon to perform an MRI-guided cryosurgery procedure more safely and conveniently than heretofore possible. Since the Control unit 45 of the cryosurgery device is located externally to the MRI room, it is not influenced by the magnetic field of the MRI magnet, and further does not interfere with the imaging results. Further, the present invention discloses a novel configuration wherein the MRI magnet includes channels for installation of connecting tubes therein so as to enable to directly connect the operating members 2 to the MRI magnet, thereby enabling a surgeon to conveniently and safely handle the operating members.

While the invention has been described with respect to a limited number of embodiments, it will be appreciated that many variations, modifications and other applications of the invention may be made.

What is claimed is:

1. A system for MRI-guided surgery, comprising:
   (a) an MRI magnet for accommodating a patient, said MRI magnet being positionable within an MRI room, said MRI magnet having at least one opening for enabling access of a surgeon to the patient, said MRI magnet including at least one channel extending therethrough for receiving a line member of a surgical device;
   (b) a surgical device, including:
      (i) an operating member for operating the patient;
      (ii) a control member for controlling said operating member, said control member being positionable externally to the MRI room;
      (iii) a line member having a first end connectable to said operating member and a second end connectable to said control member, said line member being of a length allowing positioning of said MRI magnet in the MRI room and said control member externally thereto, at least a portion of said line member is received within said channel of said MRI magnet;
   thereby, enabling a surgeon to operate both said MRI magnet and said surgical device from within the MRI room.

2. The system of claim 1, wherein said MRI magnet includes an interface member for connecting said operating member to said portion of said line member received within said channel.

3. The system of claim 1, wherein said operating member is a cryogenic probe including a Joule-Thomson heat exchanger, said line member is a gas tube, and said control member includes a gas container for providing high pressure gas to said cryogenic probe via said gas tube.

4. The system of claim 3, wherein said control member includes a microprocessor for controlling the operation of said surgical device.

5. The system of claim 4, further including a display member positionable within said MRI room, said display member being electrically connected to said microprocessor for providing information relating to the operation of said surgical device.

6. The system of claim 4, wherein said cryogenic probe includes a thermal sensor electrically connected to said microprocessor.

7. The system of claim 4, wherein said cryogenic probe includes at least one switching element for controlling the operation of said cryogenic probe, said at least one switching element being electrically connected to said microprocessor.

8. A method of MRI-guided cryosurgery, comprising:
   (a) providing a cryosurgery device, including:
      (i) a cryogenic probe for operating a patient included, said cryogenic probe including a Joule Thomson heat exchanger;
      (ii) a control member for controlling the operation of said cryogenic probe, said control member including a gas container for providing high pressure gas to said cryogenic probe; and
      (iii) a gas tube for providing gas communication between said cryogenic probe and said gas container; and (b) locating said cryogenic probe within an MRI room, locating said control member externally to said MRI room, and locating at least a portion of said gas tube within a channel extending through an MRI magnet; and (c) co-operating said cryosurgery device and said MRI mangnet from within said MRI room to perform the MRI-guided cryosurgery.

9. The method of claim 8, further comprising the step of co-monitoring the MRI-guided cryosurgery by a display member located within said MRI room, said display member providing information relating to said cryogenic probe.

10. The method of claim 8, further comprising the step of connecting said cryogenic probe to said portion of said gas tube located within said channel by an interface element.

* * * * *